United States Patent [19]

Tsien et al.

[11] Patent Number: 5,834,436
[45] Date of Patent: Nov. 10, 1998

[54] MEMBRANE-PERMEANT SECOND MESSENGERS

[75] Inventors: Roger Y. Tsien, La Jolla, Calif.; Carsten Schultz, Bremen, Germany; Wenhong Li, La Jolla, Calif.

[73] Assignee: The Regents of the University of California, Oakland, Calif.

[21] Appl. No.: 475,758

[22] Filed: Jun. 7, 1995

Related U.S. Application Data

[63] Continuation-in-part of Ser. No. 45,585, Apr. 9, 1993, abandoned.

[51] Int. Cl.$^6$ .......................... A61K 31/70; C07H 15/207
[52] U.S. Cl. .................... 514/23; 514/143; 514/144; 536/1.11; 536/117; 558/156; 558/160; 568/883
[58] Field of Search ................................... 536/1.11, 117; 514/23, 144; 558/156, 160; 568/883

[56] References Cited

U.S. PATENT DOCUMENTS

| | | | |
|---|---|---|---|
| 4,515,722 | 5/1985 | Yang et al. | 260/403 |
| 4,816,570 | 3/1989 | Farquhar | 536/26.8 |
| 4,968,788 | 11/1990 | Farquhar | 536/25.31 |
| 4,988,682 | 1/1991 | Kozikiwski et al. | 514/150 |
| 5,053,399 | 10/1991 | Kozikowski et al. | 514/150 |
| 5,177,064 | 1/1993 | Bodor et al. | 514/51 |
| 5,210,263 | 5/1993 | Kozikowski et al. | 558/161 |
| 5,227,508 | 7/1993 | Kozikowski et al. | 558/155 |
| 5,428,163 | 6/1995 | Mills | 544/232 |

OTHER PUBLICATIONS

Poirot et al., "Influence of the Absolute Configuration at C–4 in the Binding of D–Myo Inositol 1,4,5 Triphosphate Analogues to the $IP_3$ Receptor" *Bioorganic &Medicinal Chem. Lett.*, 5(6), 569–572 (1995).
Fauq et al., "Probing the D–1,4,5–$IP_3$/D–1,3,4,5–$IP_4$ Functional Interface. Synthesis and Pharmacology of Novel D–3–Modified myo–Inositol Trisphosphate Analogues," *J. Chem. Soc. Chem. Comm.*, (11), 1301–1302 (7 Jun. 1994).
Seewald et al., "Synthesis of D–3–Deoxy–myo–Inositol 1,4,5–Trisphosphate and its Effect on $Ca^{2+}$ Release in the NIH 3T3 Cells," *J. Chem. Soc. Chem. Comm.*, (22), 1638–1639 (15 Nov. 1990).
Kozikowski et al. (IV), "Deoxygenated Inositol 1,4,5–Trisphosphate Analogues and Their Interaction with Metabolic Enzymes. (1R,2S,4R)–Cyclohexane–1,2,4–tris(methylene-sulfonate): A Potent Selective 5–Phosphate Inhibitor," *J. Medicinal Chem.* 36(20), 3035–3038 (1993).
Kozikowski et al. (V), "Synthesis of ID–3–Deoxy–, ID–2,3–Dideoxy–2, and ID–2,3,6–Trideoxy–myo–inositol 1,4,5–Trisphosphate from Quebrachitol, Their Binding Affinities, and Calcium Release Activity," *J. Am. Chem. Soc.*, 115(11), 4429–4434.

Schultz et al., "Membrane–Permeant Derivatives of Inositol Polyphosphates Applied to REF–52 Fibroblasts," *The FASEB Journal*, (1992), p. A1924, Abstract No. 5819.
Schultz et al., "Acetoxymethyl esters of phosphates, enhancements of the permeability and potency of cAMP," *J. Biol. Chem.*, vol. 268, No. 9, pp. 6316–6322, 1993.
Tien, R.Y., "Intracellular signal transduction in four dimensions: from molecular design to physiology," *Am. J. Physiology*, vol. 32, No. 4, C723–C728, 1992.
Various Abstracts: Signal transduction: phosphoinositides and calcium, *The FASEB Journal*, abstracts 5718–5723, 1992.
Berridge et al., "Inositol phosphates and cell signalling," *Nature*, vol. 341, 197–205, 1989.
Shears, S.B., "Metabolism of the inositol phosphates produced upon receptor activation," *Biochem. J.* (1989) 260, 313–324.
Kaplan, A.T., "A possible role for inositool tetrakisphosphate as a negative regulator of calcium–related epithelial chloride secretion," Abstract Form for Aemrican Gastroenterological Association, May 1992.
Farquhar et al., "Biologically–reversible phosphate–protective groups," *J. Pharm. Sci.*, vol. 72, No. 3, 1983.
Srivastva et al, "Bioreversible phosphate protective groups: synthesis and stability of model acyloxymethyl phosphates," *Bioorganic Chem.*, 12, 118–129 (1984).

*Primary Examiner*—John Kight
*Assistant Examiner*—L. Eric Crane
*Attorney, Agent, or Firm*—Oppenheimer Poms Smith

[57] ABSTRACT

Acyloxyalkyl esters of phosphate-containing second messengers which are capable of permeating cell membranes. Once inside the cell, the ester derivatives undergo enzymatic conversion to the biologically active form of the second messenger. The acyloxyalkyl esters have the formula:

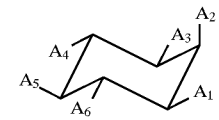

wherein $A_1$ to $A_6$ is H, OH, F or

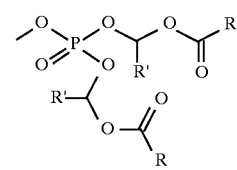

wherein R is an alkyl group having from 2 to 6 carbon atoms and R' is H or $CH_3$ or R is $CH_3$ and R' is $CH_3$ and wherein at least one of $A_1$ to $A_6$ is a phosphoester having the formula set forth above.

20 Claims, 6 Drawing Sheets

FIG. 1

FIG. 2A  bt₂cAMP/AM INITIATES CL⁻-SECRETION OF T₈₄-CELLS.

1a – 5a : $X_1 = X_2 = X_3 = OBn$, $X_4 = OH$
1b – 5b : $X_1 = X_2 = X_3 = X_4 = H$
1c – 5c : $X_1 = X_2 = X_3 = X_4 = F$
1d – 5d : $X_1 = OH$, $X_2 = OP(O)(OH)_2$, $X_3 = X_4 = OP(O)(OCHR'OCOR)_2$

MEMBRANE-PERMEANT SECOND MESSENGERS

This is a continuation-in-part of application Ser. No. 08/045,585, filed Apr. 9, 1993, now abandoned.

This invention was made with Government support under Grant No. NS-27177, awarded by the National Institute of Health. The Government has certain rights in this invention.

BACKGROUND OF THE INVENTION

1. Field of the Invention

The present invention relates generally to biologically important phosphates such as second messengers. More particularly, the present invention relates to modifying second messengers to form derivatives which can be introduced into a cell without disrupting the cell membrane. Once inside the cell, the derivative is converted back to the biologically active second messenger.

2. Description of Related Art

The publications and other reference materials referred to herein to describe the background of the invention and to provide additional detail regarding its practice are hereby incorporated by reference. For convenience, the reference materials are numerically reference and grouped in the appended bibliography.

Second messengers are ions or small molecules that carry information from the cell membrane to targets on the inside of the cell. They play a major role in biological signal transduction and amplification (1). A common feature of most of the known second messengers, such as adenosine 3',5'-cyclic monophosphate (cAMP) (2,3), guanosine 3',5'-cyclic monophosphate (4) (cGMP), myo-inositol-1,4,5-triphosphate $(1,4,5)IP_3)$ or myo-inositol-1,3,4,5-tetrakisphosphate $(1,3,4,5)IP_4)$ (5), is the presence of phosphates. The correct number and position of these phosphates is essential for biological specificity and also confers extreme hydrophilicity (6,7).

The hydrophilicity of second messengers prevents endogenously generated molecules from leaking out of cells. As a result, high sensitivity is maintained within the responding cell and freedom from cross-talk between neighboring cells is achieved. However, the membrane impermeability of second messengers also makes deliberate extracellular application difficult or ineffective (2,6,8), even though such intervention would often be very useful for research or therapeutic reasons.

One approach for introducing phosphate containing compounds into cells involves using protective groups to reversibly convert the negatively charged phosphate compound into a neutral compound for transport through the cell membrane. The protective group is chosen so that it is enzymatically cleaved from the phosphate compound inside the cell to produce the original phosphate compound. For example, lipophilic, intracellularly hydrolyzable derivatives have been useful for amino, hydroxyl, and carboxylate moieties (9–12). Acetoxymethyl (AM) esters of polycarboxylate cation indicators and chelators are have also been used (12–14). Analogous acyloxyalkyl esters applied to phosphates are known, but they have been less widely exploited (15).

On simple model phosphates, uses of AM esters have been limited to potential therapeutic drugs, such as phosphonoformate (foscarnet) (16), antiviral nucleotides such as 5-fluoro-2'-deoxyuridine monophosphate (17,18), and a 3-phosphonate-containing inhibitor of the insulin receptor kinase (19). The phosphonoformate esters proved not to be biologically useful due to failure to hydrolyze to the correct products (16), but esterification was found to enhance the effectiveness of the antiviral nucleotides and kinase inhibitor (17–19).

Considerable work has been done on o-nitrobenzyl esters as photolyzable ("caged") derivatives of ATP (20), cyclic nucleotides (21,22), and inositol phosphates (23). However, the emphasis has been on producing a kinetically fast and complete transition from a monoester to the active freed phosphate metabolite (24,25), rather than as a general means of achieving membrane permeability. In addition, nitrobenzyl esters become cumbersome if more than one are required to mask negative charges, because multiple groups add considerable bulk and require high doses of UV to cause cleavage of all the groups.

Although numerous different myo-inositol polyphosphates are possible, only about a dozen have been found in cells. Their intracellular functions are controversial or unknown, except for myo-inositol 1,4,5-triphosphate ($IP_3$), whose role as an intracellular second messenger to release $Ca^{2+}$ from internal stores is unquestioned (26). The next most studied inositol polyphosphate is myo-inositol 1,3,4,5-tetrakisphosphate ($IP_4$), which is believed to cooperate with $IP_3$ to open $Ca^{2+}$-channels in the plasma membrane (27–30) or to resequester $Ca^{2+}$ released by $IP_3$ (31,32). However, these hypotheses remain controversial (33–37).

Almost nothing is known about intracellular functions for other inositol polyphosphates. Detailed dissection of the roles of inositol polyphosphates is often difficult if they are endogenously generated in response to agonists, since such stimulation may affect multiple receptors, G proteins, diacylglycerol formation, multiple inositol polyphosphates, and yet other transduction pathways. Direct introduction of specific inositol polyphosphates is often preferable.

The high negative charge of inositol polyphosphates results in negligible passive permeability through membranes. Existing methods for introducing inositol phosphates include microinjection, patch-clamp techniques, and permeabilization by electroporation, detergents like saponin, or removal of extracellular $Ca^{2+}$. All these methods breach the plasma membrane and jeopardize the more complex functions and long-term viability of the cells. Furthermore, microinjection and patch techniques can only be applied to a few cells at a time.

In view of the above, there is a need to provide a procedure for increasing the membrane permeability of second messengers so that they can be introduced effectively into cells in amounts which are useful for investigational or therapeutic purposes.

SUMMARY OF THE INVENTION

In accordance with the present invention, compositions and methods are provided for increasing the permeability of phosphate-containing second messengers into a cell without disrupting the cell membrane. The invention involves esterifying the phosphate groups present in the second messenger molecule to form an acyloxyalkyl ester derivative. The acyloxyalkyl ester of the second messenger has a neutral charge and therefor can permeate into the cell without disrupting the cell membrane. Once inside the cell, the esters are cleaved to convert the molecule back to its biologically active form. Acetoxymethyl esters worked well for cyclic nucleotide esters but proved insufficiently hydrophobic for inositol phosphates. Propionyloxymethyl and butyryloxymethyl esters are preferred for the latter class.

As a further optional feature of the present invention, hydroxyl groups which are present in the second messenger molecule are masked to aid in synthesis of the derivatives and further enhance the permeability of the second messenger derivative into the cell. The hydroxyl groups are masked with an acyl group (1–4 carbon atoms) which can be easily cleaved once the modified second messenger enters the cell. Butyryl groups were found to provide optimum masking while still being easily cleaved by cell enzymes.

As a further feature of the present invention, 8-substituted cyclic nucleotides are esterified and acylated to increase their permeability into cells. These synthetic nucleotides are useful for investigational and therapeutic purposes. The increase in permeability provided by the present invention provides a convenient procedure for introducing the 8-substituted cyclic nucleotides into cells.

As one aspect of the present invention, the phosphate and hydroxy groups of cyclic nucleotides, such as cAMP and cGMP, are esterified and acylated to form neutral derivatives. These neutral derivatives were found to cross the cell membrane and to be converted into their active form once inside the cell. The introduction of cAMP and/or cGMP into a cell is useful for both investigational and therapeutic purposes.

Another aspect of the present invention involves the esterification of second messengers such as, inositol triphosphate and inositol tetraphosphate.

The resulting neutral derivatives were also found to permeate into cells and were converted back into their active forms once inside the cell. The introduction of inositol phosphates into cell is also useful for both investigational and therapeutic purposes.

We discovered that esterification of the inositol phosphates with acetoxymethyl groups did not provide a sufficient increase in cell permeability to be useful. We discovered that more hydrophobic esters were required. Replacement of acetoxymethyl groups with propionyloxymethyl and butyryloxymethyl groups produces inositol phosphate esters which have much greater cell permeability rates while still being amenable to intracellular cleavage to form the active inositol phosphate. Inositol phosphates which have this high degree of cell permeability include those having the formula wherein $A_1$ to $A_6$ is H, OH, F or wherein R is an alkyl group having from 2 to 6 carbon atoms and R' is H or $CH_3$ or R is $CH_3$ and R' is $CH_3$ and wherein at least one of $A_1$ to $A_6$ is a phosphoester having the formula set forth above.

The above described and many other features and attendant advantages of the present invention will become better understood by reference to the following description when taken in conjunction with the accompanying drawings.

DESCRIPTION OF THE PREFERRED EMBODIMENTS

The present invention is directed to modifying second messengers and derivatives thereof which contain phosphates so that they can be easily introduced into a cell without disrupting the cell membrane. The invention involves esterifying the phosphate groups present in the second messenger to form a neutral acyloxyalkyl derivative which can readily diffuse through the cell membrane. The acyl group may contain up to 6 carbon atoms and is located at the 1 position of the alkyl group. The alkyl group may contain up to 7 carbon atoms. It was found for cAMP and cGMP that acetoxymethyl esters provide optimum cell membrane transport while still being amendable to cleavage from the second messenger after entry into the cell. Acetoxymethyl esters of inositol phosphates were found not to be optimally cell permeable. For second messengers having multiple phosphate groups, it is preferred that all of phosphate groups be masked as propionyloxymethyl or butyryloxymethyl esters.

The present invention is applicable to increasing the cell permeability of a wide variety of phosphate-containing second messengers and derivatives thereof.

Preferred exemplary phosphate-containing second messengers include cAMP, cGMP, 1,4,5 $IP_3$, 1,3,4,5 $IP_4$ and myo-inositol 3,4,5,6-tetrakisphosphate. The present invention is also applicable to derivatives of cyclic nucleotides. Exemplary derivatives include the 8-substituted derivatives of cAMP or cGMP. The 8-substituted derivatives include 8-bromo-cAMP or cGMP, 8-chloro-cAMP or cGMP and 8-para-chlorophenylthio (cCPT) cAMP or cGMP.

It is preferred for cAMP and cGMP that the hydroxyl groups of the phosphate-containing second messengers be masked or protected during synthesis. Masking with acyl groups having up to 4 carbon atoms is preferred. Larger acyl groups are not preferred because they are more difficult for the cell to cleave from the second messenger.

Examples of practice showing the synthesis and use of cAMP/cGMP acetoxymethyl esters in accordance with the present invention are as follows:

Proton and $^{31}$P NMR spectra were obtained in CDCl$_3$, with residual CHCl$_3$ ($\delta$=7.26), being used as the internal standard for $^1$H spectra. 85% phosphoric acid was used as an external standard for $^{31}$P spectra. All NMR spectra were recorded on either a Varian Gemini-200 (200 MHz) or a General Electric QE-300 (300 MHz) spectrometer and are reported with the following abbreviations: s, singlet; d, doublet; t, triplet; dd, doublet of doublets; m, complex multiplet. Fast atom bombardment mass spectroscopy (with glycerol as matrix) and precise mass determinations were performed by the mass spectroscopy facility of the University of California, Riverside. Capillary electrophoresis was performed on a Dionex CES.

Pyridine and acetonitrile used in the synthesis were stored over activated molecular sieve (3 Å) for at least 3 d. All other solvents were purchased in highest purity available and were used as received. N,N-Diisopropylethylamine (DIEA) was distilled from CaH$_2$. Acetoxymethyl bromide (AM-Br) was prepared according to known procedures (38). All nucleotides were from Sigma. Phenylphosphonic acid was from Fluka, Switzerland. 4-Methylumbelliferylphosphate was from Boehringer, FRG. All other reagents were from Aldrich.

The compounds shown in Table 1 were synthesized as set forth below: Compounds 1–3 were synthesized for comparative purposes. Compounds 4 a/b (cAMP/AM) and 5 a/b (cGMP/AM) are preferred exemplary compounds in accordance with the present invention.

Synthesis of 4-Methylumbelliferyl Phosphate Bis(acetoxymethyl)ester (1)-The dilithium salt of 4-methylumbelliferyl phosphate (200 mg, 0.74 mmol) was dissolved in water and a concentrated solution of silver acetate was added. The disilver 4-methylumbelliferyl phosphate precipitated immediately and was filtered, washed with water and dried to a shining silver-white powder (yield: 277 mg, 79%). The silver salt (60 mg, 0.13 mmol) was suspended in 1 mL dry CH$_3$CN and 50 mg (0.33 mmol) AM-Br was added. At frequent intervals, the mixture was treated for 2 minutes at a time in an ultrasonic bath (Branson B-220). Frequent monitoring by $^1$H NMR showed the reaction to be complete after 4 hours. The supernatant was evaporated to dryness to yield 38 mg (72%) of 4-methylumbelliferyl phosphate bis(acetoxymethyl)ester (1); $^1$H NMR (CDCl$_3$, 200 MHz) $\delta$ 2.12 (s, 6H), 2.43 (s, 3H), 5.73 (dAB, 4H, J$_{AB}$=5.5 Hz, J$_{PH}$=14.2 Hz, —CH$_2$—), 6.27 (s, 1H, H3), 7.17–7.25 (m, 2H, H6,H8), 7.59 (m, 1H, H5); $^{31}$P NMR (CDCl$_3$, 121.5 MHz) $\delta$–9.1; MS m/z (M+H)$^+$ calcd 401.0638, obsd 401.0625.

Synthesis of Phosphate Tris(acetoxymethyl)ester (2)— Silver phosphate (30 mg, 71 μmol) was suspended in 0.5 mL dry CH$_3$CN and AM-Br (22 mg, 145 μmol) was added. After frequent sonication for 20 hours at room temperature, another 15 mg (100 μmol) AM-Br was added. When the suspended solid had lost its yellow color, the mixture was centrifuged (1000 rpm, 1 min), and the supernatant was evaporated to dryness and the residue was washed with dry

TABLE 1

Structures of Acetoxymethyl Esters of Various Organic Phosphates

| comp. | structure | counter[a] ion M* | yield[b] | $^{31}$P—NMR [ppm] |
|---|---|---|---|---|
| 1 | (structure shown) | Ag* | 72% | –9.1 |
| 2 | (structure shown) | Ag* | 98% | –2.25 |
| 3 | (structure shown) | HDIEA* | 86% | 18.70 |
| 4a/4b 5a/5b | (structure shown) BtAde(BtGua) | HDIEA* Ag* HDIEA* | 59% 52% 40% | –8.0/[c] –5.0 –5.5/[c] –8.5 |

[a]M$^+$ specifies the counter ion for the phosphate-containing starting material; HDIEA$^+$ = diisopropylethylammonium.
[b]Yield by weight unless otherwise noted.
[c]Shift values for both diastereomers.

toluene to give phosphate tris(acetoxy-methyl)ester (2) as a clear oil (yield 98%); $^1$H NMR (CDCl$_3$, 200 MHz) δ 2.15 (s, 9H), 6.45 (d, 6H, $J_{PH}$=13.5 Hz); $^{31}$P NMR (CDCl$_3$, 121.5 MHz) δ−2.25; MS m/z 241 (M-CH$_2$OAc)$^-$.

Synthesis of Phenylphosphonate Bis(acetoxy-methyl) ester (3)—Phenylphosphonic acid (31.6 mg, 0.2 mmol) and diisopropylethylamine (DIEA, 130 mg, 1.0 mmol) were dissolved in 1 mL dry CH$_3$CN. AM-Br (77 mg, 0.5 mmol) was added and the solution was stirred at room temperature over night. After evaporation of the solvent the solid residue was extracted with dry toluene. Purification of the crude product 3 was performed on a Si60 column (10×40 mm) with 75% toluene/25% ethyl acetate to yield 52 mg 3 (86%) as a clear oil. $^1$H NMR (CDCl$_3$, 200 MHz) δ 1.95 (s, 6H), 5.66 (dAB, 4H, $J_{AB}$=5.3 Hz, $J_{PH}$=13.8 Hz, —CH$_2$—), 7.30–7.55 (m, 3H), 7.70 (m, 2H). $^{31}$P NMR (toluene-d$_8$, 121.5 MHz) δ 18.70.

Synthesis of N$^6$,O$^{2'}$-Dibutyryl Adenosine 3',5'-cyclic Monophosphate Acetoxymethyl Ester -bt$_2$cAMP/AM (4a/4b)—Two different methods were used to synthesize bt$_2$cAMP/AM. Method A: The sodium salt of N$^6$,O$^{2'}$-dibutyryl cAMP (12.5 mg, 25 μmol) was dissolved in 1 mL MeOH—H$_2$O (1:1) and passed through a Dowex 50W-X8 column (10×40 mm, H$^+$-form). The free acid was eluted with 15 mL 50% MeOH. After evaporating to dryness, DIEA (6 mg, 50 μmol) and 1 mL dry CH$_3$CN were added. The reaction was started by the addition of AM-Br (16 mg, 94 μmol). After stirring the solution at room temperature for 4 days, the reaction mixture was chromatographed directly on a Si60 column (10×40 mm, 230–400 mesh) with 95% CH$_3$CN/5% hexane as the eluent under slight pressure. The eluant was collected in 5 mL fractions. Fractions 5–7 contained 5.3 mg (38% yield) of the faster eluting diastereomer of dibutyryl cAMP acetoxymethyl ester (4a) in high purity. $^1$H NMR (CDCl$_3$, 300 MHz) δ 1.05 (t, 3H, J=7.0 Hz), 1.12 (t, 3H, J=7.0 Hz), 1.74 (m, 2H), 1.84 (m, 2H), 2.20 (s, 3H), 2.51 (m, 2H), 2.95 (t, 2H, J=7.0 Hz), 4.36 (ddd, 1H, J=2.7, 10.1, 10.1 Hz, H4'), 4.49 (dd, 1H, J=10.0, 10.0 Hz, H5'$_{ax}$), 4.66 (dddd, 1H, J=2.7, 10.0, 10.0, 22.1 Hz, H5'$_{eq}$), 5.67–5.95 (m, 4H, —CH$_2$—, H2', H3'), 6.04 (s, 1H, H1'), 8.01 (s, 1H, H2), 8.49 (broad s, 1H, N$^6$H), 8.78 (s, 1H, H8); $^{31}$P NMR (CDCl$_3$, 121.5 MHz) δ−5.0 ppm.

Fractions 8+9 yielded 8.7 mg of a clear oil which contained diisopropylethylammonium bromide and the slower eluting diastereomer of 4b (2:1 w/w as determined by NMR, yield 2.9 mg 4b, 21% from dibutyryl-cAMP). $^1$H NMR (CDCl$_3$, 200 MHz), δ 0.99 (t, 3H, J=7.0 Hz), 1.05 (t, 3H, J=7.5 Hz), 1.70 (m, 4H), 2.18 (s, 3H), 2.45 (t, 2H, J=7.0 Hz), 2.89 (t, 2H, J=7.5 Hz), 4.40–4.70 (m, 3H, H4',H5'$_{eq}$,H5'$_{ax}$), 5.62–5.78 (AB-part of ABX, 2H, $J_{AB}$=5.1 Hz, —CH$_2$—), 5.83 (m, 2H, H2', H3'), 6.01 (s, 1H), 8.02 (broad s, 1H, H2), 8.51 (broad s, 1H, N$^6$H), 8.69 (s, 1H, H8); $^{31}$P NMR (CDCl$_3$, 121.5 MHz) δ−8.0 ppm; MS (4a/4b 1:1 mixture) m/z (M+H)$^+$calcd 542.1652, obsd 542.1681.

Method B: 58 mg (0.12 mmol) of the sodium salt of Bt$_2$cAMP was dissolved in 0.5 mL H$_2$O and 300 μL 1.8M AgNO$_3$ solution was added. The resulting white precipitate was filtered off washed with H$_2$O, and dried to yield 30.5 mg (45%, 54 μmol) of the silver salt of Bt$_2$cAMP. The white powder was suspended in 1 mL of dry CH$_3$CN and 51 mg (330 μmol) AM-Br were added. The suspension was frequently sonicated for 4 h at room temperature. The two resulting diastereomeric acetoxymethyl esters 4a and 4b were purified as described under method A to yield 2.8 mg of the fast eluting isomer 4a (10% yield) and 9.6 mg (35%) of the slow eluting diastereomer 4b. NMR and MS analysis of the products of both methods were identical.

Synthesis of N$^2$, O$^{2'}$-Dibutyryl Guanosine 3',5'-cyclic Monophosphate Acetoxymethyl Ester bt$_2$GMP/AM (5a/5b) —The sodium salt of Bt$_2$cGMP (24 mg, 47 μmol) was passed through Dowex 50W-X8 (H$^+$ form) and the free acid was eluted with 15 mL 50% MeOH. After evaporating to dryness, 1 mL dry acetonitrile, 13 mg (100 μmol) DIEA and 21 mg (135 μmol) AM-Br were added. The solution was stirred overnight, evaporated to dryness, dissolved in CH$_3$CN/hexane (95:5, v/v) and eluted over a Si60 column (10×40 mm) to yield 11 mg (40%) of the two diastereomers of dibutyryl cGMP-AM (5a/5b) as a mixture. $^1$H-NMR (5a only, CDCl$_3$, 200 MHz) δ 1.00 (m, 6H), 1.74 (m, 4H), 2.38 (s, 3H), 2.42 (m, 2H), 2.48 (m, 2H), 4.18 (ddd, 1H, J=4.0, 10.0, 10.0 Hz, H4'), 4.30–4.54 (m, 2H, H5'$_{ax}$, H5'$_{eq}$), 5.13 (ddd, 1H, J=1.8, 4.1, 10.0 Hz, H3'), 5.56 (dd, 1H, J=4.1, 4.1 Hz, H2'), 5.71 (dAB, 2H, J=12.5, 9.1 Hz, —CH$_2$—), 6.04 (d, 1H, J=4.0 Hz, H1'), 7.65 (broad s, 1H, N$^2$H), 10.14 (s, 1H, H8), 12.30 (broad s, 1H, N$^1$H); $^{31}$P NMR (CDCl$_3$, 121.5 MHz) δ−5.5 and −8.5 ppm; MS m/z (M+H)$^+$calcd 558.1601, obsd 558.1611.

The most general and economical synthetic route to acetoxymethyl phosphate esters is believed to be alkylation of the parent phosphate anions by acetoxymethyl halides. The instability of acetoxymethanol precludes its phosphorylation. Preliminary synthetic attempts, similar to the experiments of Srivasta and Farquhar (15), were performed on 4-methylumbelliferyl phosphate and phenyl phosphonate as readily available model compounds detectable by UV absorption and bearing no competing nucleophilic centers. 4-Methylumbelliferyl phosphate bis(acetoxymethyl)ester (Table I-1) was successfully prepared in 73% yield by suspending the disilver salt of 4-methylumbelliferyl phosphate in dry acetonitrile, adding acetoxymethyl bromide (AM-Br) (38), and sonicating the heterogeneous mixture at frequent intervals for 24 hours. The $^1$H NMR of the supernatant showed an AB doublet at 5.7 ppm for the methylene group of the acetoxymethyl ester, a typical pattern for all phosphate acetoxymethyl esters reported here. The synthesis of phosphate tris(acetoxymethyl)ester (Table I-2) offered a possibility to directly monitor the progress of the reaction. Yellow Ag$_3$PO$_4$ was reacted with AM-Br as described above. Disappearance of the color after 36 hours indicated completion of the reaction. The product was the only compound in the organic phase (98% yield).

An alternative to silver salts is desirable for polyphosphates or molecules bearing oxidizable functionalities. Direct treatment of phenylphosphonic acid with an excess of the hindered base diisopropylethylamine (DIEA) and AM-Br eventually gave an 86% yield of the phenylphosphonate bis(acetoxy-methyl)ester (Table I-3).

Analogous reactions worked, albeit in lower yield, for N$^6$,2'-O-dibutyryl adenosine 3',5'-cyclic monophosphate acetoxymethyl ester (Bt$_2$cAMP/AM, 4a/4b) and N$^2$,2'-O-dibutyryl guanosine 3',5'-cyclic monophosphate acetoxymethyl ester (Bt$_2$cGMP/AM, 5a/5b). The commercially available sodium salts of Bt$_2$cAMP and Bt$_2$cGMP were converted into the free acids on Dowex 50W-X8 and then into DIEA salts. Reaction took place in dry CH$_3$CN with an excess of DIEA and AM-Br for 5 days at room temperature. Both nucleotide AM-esters were purified on silica gel 60 (CH$_3$CN/hexane 19:1 v/v) after evaporation of the solvent. The two diastereomers of Bt$_2$cAMP/AM (4a/4b) were isolated in yields of 37% and 21% for the fast and slow-eluting isomers, the latter co-eluting with residual DIEA. $^{31}$P-NMR resonances were −5.0 ppm and −8.0 ppm, respectively, but absolute configurations were not determined. The analogous two diastereomers of Bt$_2$cGMP/AM (5a/5b) could not be separated under the described conditions, but were free of DIEA. Bt$_2$cAMP/AM was also prepared by alkylating the silver salt of Bt$_2$cAMP with AM-Br in CH$_3$CN with frequent sonication for 24 h. These heterogeneous conditions reversed the enantiomeric preference, giving the fast and slow-migrating isomers in 10% and 35% yields.

Figure 8:
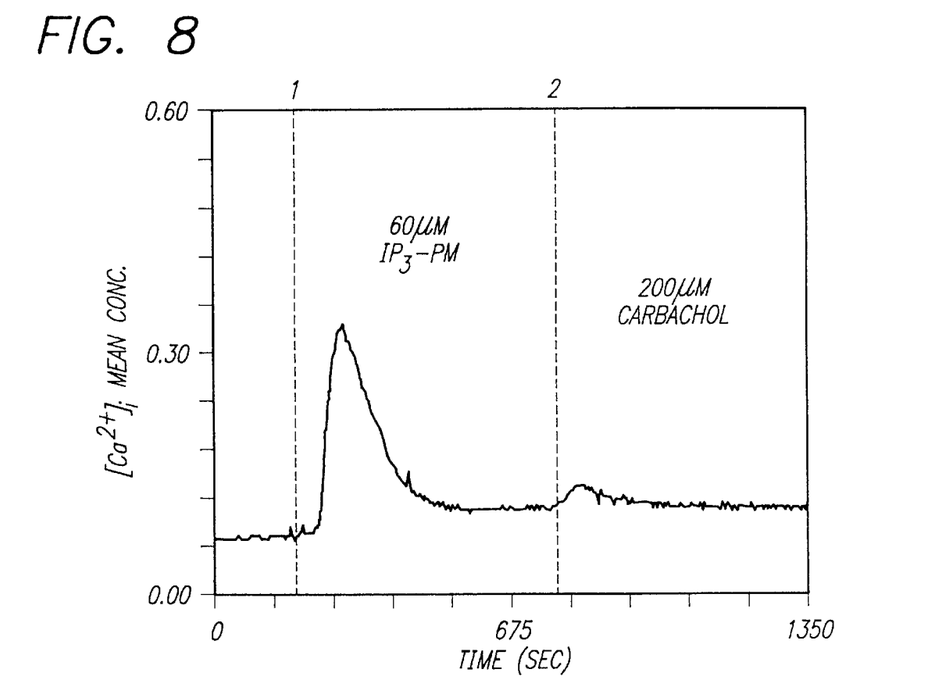
FIG. 8 depicts test results showing permeation of $IP_3$/PM at a dose of 60 $\mu$m into astrocytoma cells in a medium lacking extracellular $Ca_2+$.

The synthesis of cAMP and cGMP described above utilizes butyryl groups to mask or protect the hydroxyl groups. This is because the direct conversion of a cAMP or cGMP into their acetoxy esters yields only minute amounts of product. Trimethylsilyl (TMS) groups were also found to work well as a protective group. The synthesis schemes for direct and TMS protected synthesis is shown in FIG. 8.

Synthesis of the acetoxy ester of cAMP using TMS is set forth below:

General Methods—Proton and $^{31}$P NMR spectra were obtained in CDCl$_3$ with residual CHCl$_3$ ($\delta$=7.26), being used as the internal standard for $^1$H spectra. 85% phosphoric acid was used as an external standard for $^{31}$P spectra. All NMR spectra were recorded on either a Varian Gemini-200 (200 MHz) or a General Electric QE-300 (300 MHz) spectrometer and are reported with the same abbreviations as in the preceding examples.

Acetonitrile were stored over activated molecular sieve (3 Å) for at least 3 d. All other solvents were purchased in highest purity available and were used as received. N,N-Diisopropylethylamine (DIEA) was distilled from CaH$_2$. Acetoxymethyl bromide (AM-Br) was prepared according to known procedures. cGMP was from ICN or Calbiochem. All other nucleotides were from Sigma. All other reagents were from Aldrich.

Figure 4:
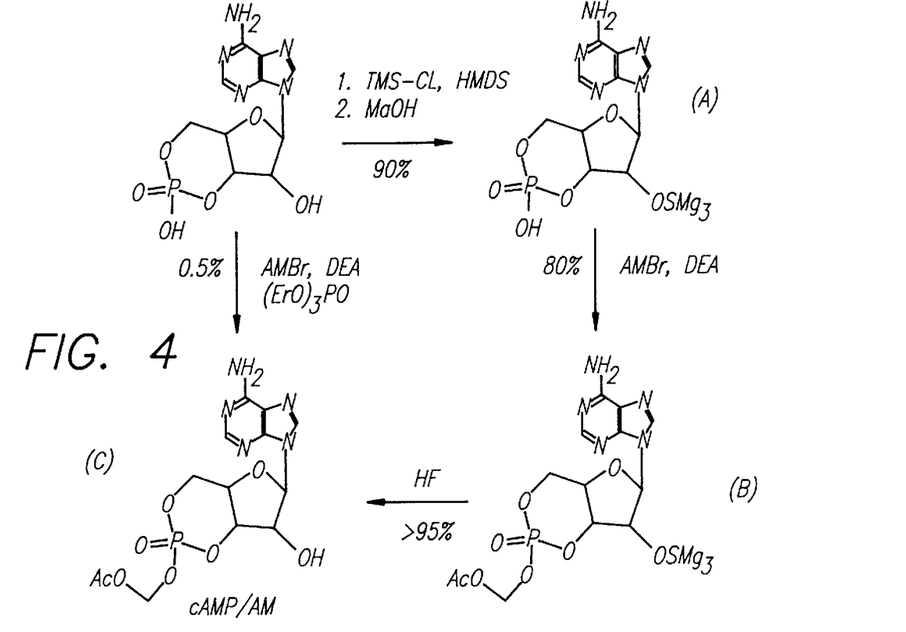
FIG. 4 depicts the synthesis scheme preparing 3',5'-cyclic monophosphate acetoxymethyl ester.

The following three step synthesis is outlined in FIG. 4.

Synthesis of 2'-O-Trimethylsilyl Adenosine 3',5'-cyclic Phosphate (FIG. 4-A)—The free acid of cAMP (50 mg, 0.15 mmol) was suspended in 3 mL dry DIEA. One (1) mL Hexamethyldisilazane (HMDS) and 0.5 mL Trimethylsilyl chloride (TMS-Cl) were added under Ar and the mixture was heated to 100° C. for 3 hours. After cooling to r.t. all volatile components were evaporated off in high vacuum. The residual oil was extracted with 2×2 mL dry toluene. A sample of the extract, exclusively containing N$^6$, 2'-O-di(trimethylsilyl) adenosine 3',5'-cyclic monophosphate trimethylsilyl ester, was evaporated to dryness and analyzed by NMR: $^1$H NMR (toluene-d$_g$, 200 MHz) diastereomer 1 (80%) $\delta$ 0.32 (s, 9H), 0.45 (s, 9H), 0.47 (s, 9H), 4.15–4.61 (m, 3H, H4', H5'$_{eq}$, H5'$_{ax}$), 4,98 (d, 1H, J=4.7 Hz, H2'), 5.60 (s, 1H, N$^6$H), 5.74 (ddd, 1H, J=1.6, 4.7, 9.5 Hz, H3'), 5,83 s, 1H, H1'), 7.64 (s, 1H, H2), 8.6 (s, 1H, H8). Diastereomer 2 (20%) $\delta$ 4.65 (d, 1H, J=4.2 Hz, H2'), 5.20 (m, 1H, H3'), 5.66 (s, 1H, N$^6$H), 6.05 (s, 1H, H1'), 7.77 (s, 1H, H2), 8.58 (s, 1H, H8). The toluene extract was treated with 12 μL MeOH (0.3 mmol) for 3 min. followed by rapid evaporation of the solvents. The remaining white solid fairly pure 2'-O-TMS-cAMP (1). $^1$H NMR (CD, OD, 200 MHz) $\delta$ 0.80 (s, 9H, TMS), 4.32 (m, 3H, H4', H5'), 4.65 (d, 1H, J=8.2 Hz, H2'), 4.95 (m, 1H H3'), 6.12 (s, 1H, H1'), 7.16 (broad s, 2H, NH$_2$), 8.40, 8.45 (2s, 1H each, H2, H8). $^{31}$H-NMR O.

Synthesis of 2'-O-Trimethylsilyl Adenosine 3'5'-cyclic Monophosphate Acetoxymethyl Ester (FIG. 4-B)—25 mg (0.062 mmol) 2'-TMS-cAMP (1) was dissolved in 0.5 mL dry CH$_3$CN containing 0.05 mL DIEA (0.28 mmol) under Ar and 0.028 mL (0.28 mmol) AMBr were added. The mixture was stirred for 3 days at r.t. then evaporated to dryness. The crude produce was purified on a Si60 column (4×1.5 cm) with dry CH$_3$CN saturated with hexane as the eluent. Prior to the separation the column was washed with the same eluent containing 0.1% acetic acid followed by the eluent alone. Most of the 2'-O-TMS-cAMP/AM (2) eluated just before HDIEA$^+$Br to yield 20.5 mg (0.042 mmol, 68%). The product consisted of 90% of one of the R$_p$/S$_p$-diastereomers, as determined by $^{31}$P NMR. $^1$H NMR (CDCl$_3$, 300 MHz) $\delta$ 0.22 (s, 9H, TMS), 2.16 (s, 3H, —OCCH$_3$), 4.43 (m, 2H, H4', H5'$_{ax}$), 4.64 (m, 1H, H5'$_{eq}$), 4.85 (d, 1H, J=5.2 Hz, H2'), 5.34 (m, 1H, H3'), 5.74 (d, 2H, J=13.1 Hz, —CH$_2$—OAc), 4.86 (broad s, 2H, NH$_2$), 5.91 (s, 1H, H1'), 7.87 and 8.41 (2s, 1H each, H2and H8). $^{31}$P NMR (CDCl$_3$, 121.5 Hz) $\delta$–7.58 (90%), –4.62 (10%).

Synthesis of Adenosine 3',5'-cyclic Monophosphate Acetoxymethyl Ester (FIG. 4-C)—14 mg (0.029 mmol) of 2 were dissolved in 1 mL of a 1:1 (v/vO mixture of CHCl$_3$/CH$_3$CN and 2 μL HF (49%) was added. The mixture was gently swirled for 2 min. before the solvents were evaporated off to quantitatively yield cAMP/AM (3) as a white solid. $^1$HNMR (CD$_3$OD, 300 MHz) $\delta$ 2.17 (s, 3H, —OAc), 4.48 (ddd, 1H, J=3.6, 9.5, 9.5 Hz, H4'), 4.50 (m, 1H, H5'$_{ax}$), 4.74 (m, 1H, H5'$_{eq}$), 5.33 (ddd, 1H, J=1.0, 4.8, 12.3 Hz, H3'), 5.75 (m, 2H, —CH$_2$—OAc), 6.15 (s, 1H, H1'), 8.41 and 8.42 (2s, 1H each, H2, H8). $^{31}$P NMR (CD$_3$OD, 121.5 MHz) $\delta$–6.85.

The following biological tests were conducted to demonstrate the biological activity of the cAMP derivative after it passes into the cell.

Figure 1:
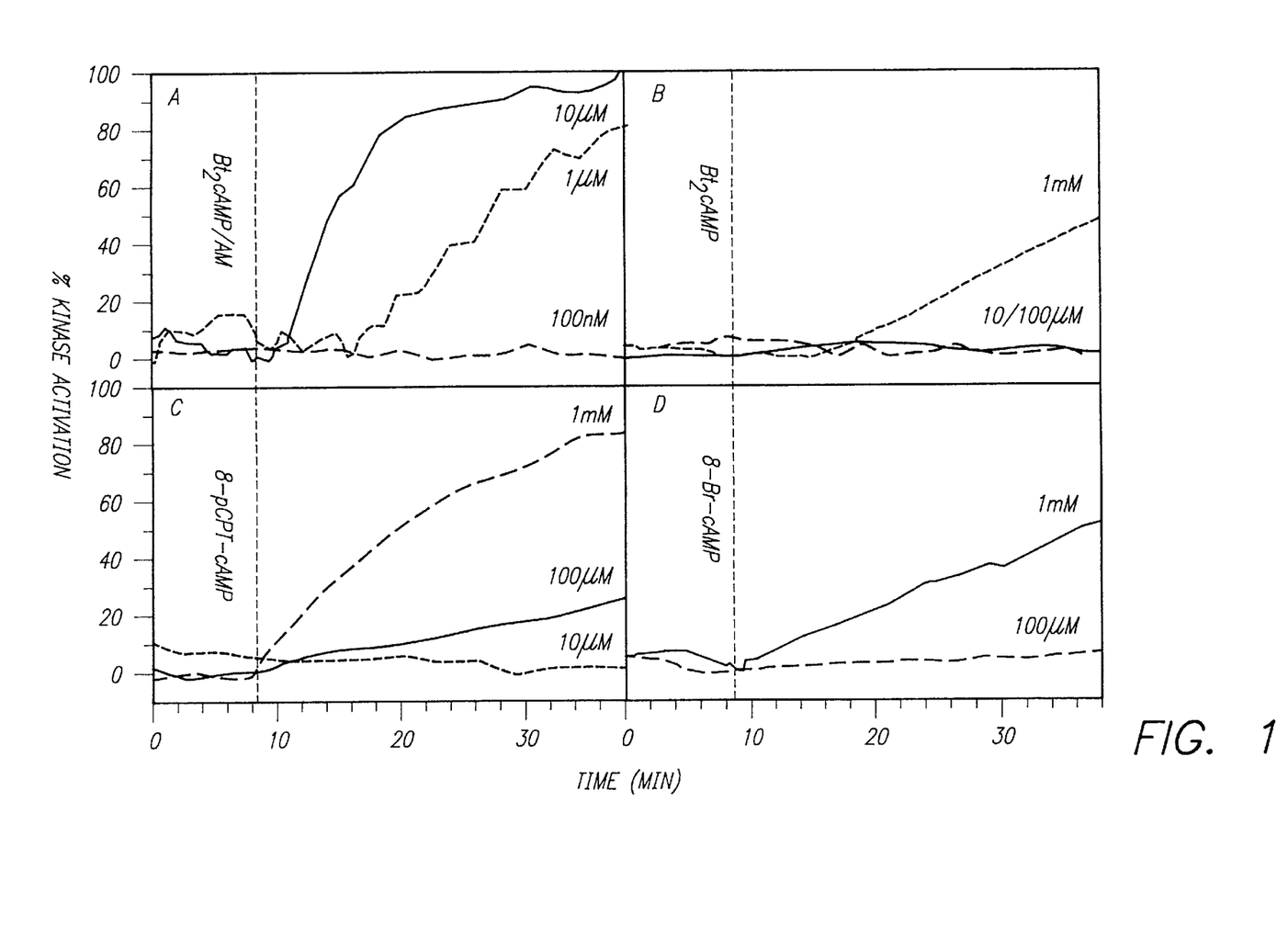
FIG. 1 is four graphic representations of the results of tests showing the kinase activation capability of $Bt_2cAMP/AM$ in comparison to other derivatives.

Activation of intracellular protein kinase A. The premier target of cAMP in most cells is the cAMP-dependent protein kinase (PKA) (45). To show that this enzyme can be activated by extracellular application of Bt$_2$cAMP/AM, we used a recently-developed assay for PKA activation in single cells (39). When PKA is doubly labeled with fluorescein on its catalytic subunits and rhodamine on its regulatory subunits to produce FICRhR, fluorescence energy transfer from the fluorescein to rhodamine occurs in the holoenzyme complex but is disrupted upon activation and dissociation of the subunits. The change in the ratio of fluorescein to rhodamine emissions parallels the increase in kinase activity and can be nondestructively imaged in single cells. REF-52 fibroblasts were microinjected with FICRhR and emission ratio images recorded at room temperature as previously described (27). 30 min after injection, 0.1, 1, or 10 μM Bt$_2$cAMP/AM were added extracellularly (FIG. 1—Graph A). The highest dose yielded a maximal change in fluorescence ratio within 15 min. The intermediate dose gave a shallower slope and a lower plateau to slightly over 50% of the maximal change. The onset of the separation of regulatory and catalytic subunit of FICRhR occurred roughly 2 min after the addition of the cAMP derivative. Much the same delay and overall time course occurred with nonesterified Bt$_2$cAMP, though much higher concentrations, 1 mM, were required (FIG. 1—Graph B). Other widely used, supposedly lipophilic cAMP derivatives showed no delay in beginning to activate PKA, but millimolar concentrations were still required (FIG. 1—Graphs C & D).

To show that intracellular enzymatic hydrolysis of the ester groups is required we examined the binding properties of Bt$_2$cAMP/AM and Bt$_2$cAMP to FICRhR in vitro. The highest concentration of Bt$_2$cAMP/AM used in the other assays (1 μM) gave no separation of the subunits, while Bt$_2$cAMP was roughly 1/100 as potent as cAMP probably due to contamination by 1% monobutyryl-cAMP as specified by the supplier (Sigma) (See Table II).

TABLE II

In-vitro cAMP-dependent kinase activation assay.

|  | cAMP |  |  | $Bt_2cAMP^a$ |  | $Bt_2cAMP/AM$ |
|---|---|---|---|---|---|---|
| concentration [μM] | 1 | 10 | $200^b$ | 10 | 10 | 10 |
| % kinase$^c$, activation | 67 | 91 | 100 | 16 | 61 | 0 |

$^a$The slight residual activity of $Bt_2cAMP$ is probably due to an impurity of $N^6$-monobutyryl cAMP (1%) as specified by the supplier.
$^b$200 μM cAMP was considered the maximal dose necessary to fully dissociate FICRhR.
$^c$Labelled cAMP-dependent kinase type I (FICRhR). This labelled isoform is more stable against subunit dissociation in the absence of cAMP at the low enzyme concentrations used in this assay than labelled type II.

Figure 2A:
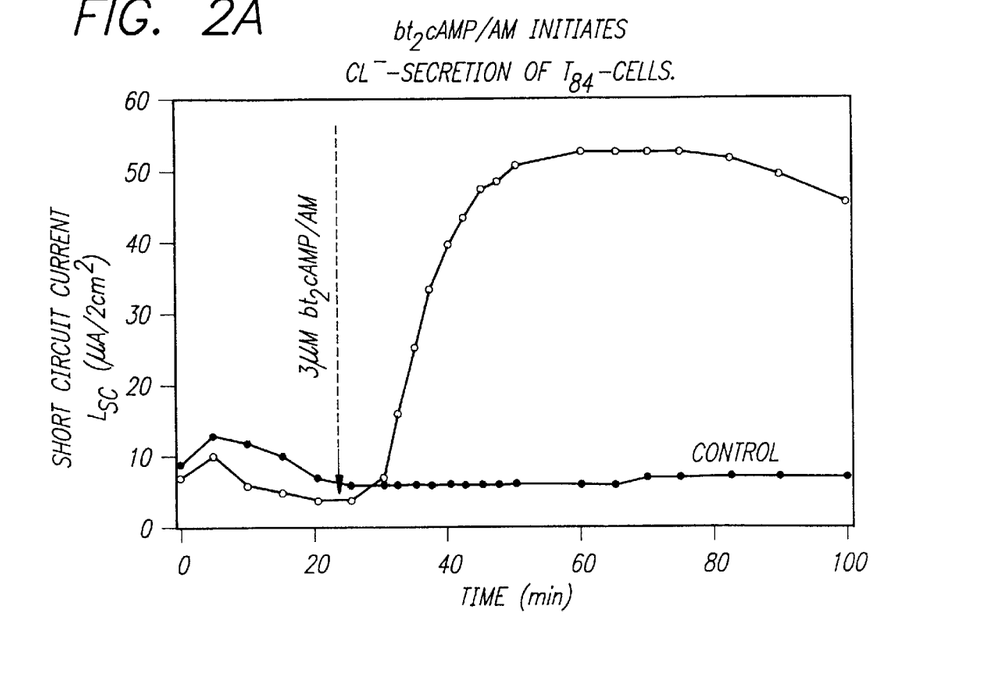
FIG. 2A is a graphic representation of the results of tests showing the initiation of $Cl^-$ secretion by $Bt_2cAMP/AM$.
Figure 2B:
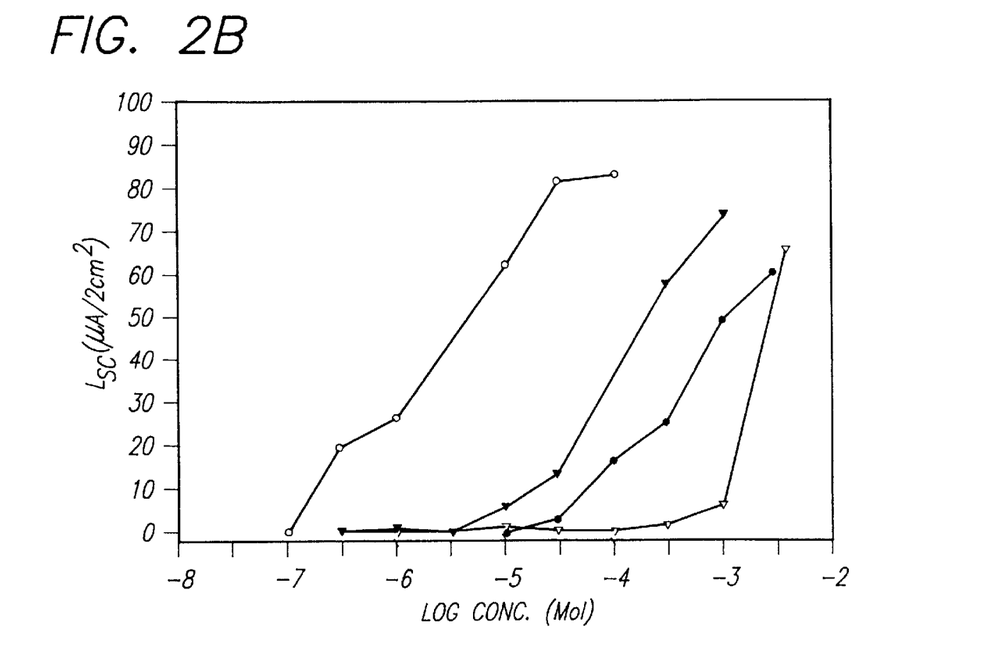
FIG. 2B is a graph showing a comparison of chloride secretion initiated by $Bt_2cAMP/AM$ and other derivatives.

One of the many well-known cell functions controlled by cAMP is intestinal transepithelial Cl$^-$-secretion (46). A convenient test system is the intestinal cell line $T_{84}$, in which chloride secretion can be continuously monitored by mounting confluent monolayers of cells in Ussing chambers (42). FIG. 2A shows the Cl$^-$-secretion measured as short circuit current ($I_{SC}$) across the cells. The addition of $Bt_2cAMP/AM$ at a concentration of 3 μM to the serosal bathing solution caused an increase in $I_{SC}$ with a maximum after 20 min. Higher concentrations of the derivative caused faster but not significantly greater responses, whereas lower concentrations reached lower maximum $I_{SC}$ values. The $I_{SC}$ values obtained at an arbitrary intermediate time, 12 min after addition of various cAMP-derivatives, were used to determine the dose dependency (FIG. 2B). The dose response curves were parallel, with $EC_{50}$ values of 2 μM and 400 μM for $Bt_2cAMP/AM$ and $Bt_2cAMP$ respectively. Therefore the introduction of the acetoxymethyl group on the phosphate increased the potency by 200 fold in this assay by circumventing the permeability barrier. Furthermore, the acetoxymethyl ester seems to be cleaved inside $T_{84}$ cells without significant delay, since the two agents gave essentially indistinguishable kinetics of activation. Tests with the cAMP-derivatives 8-Br-cAMP and 8-pCPT-cAMP showed activation of Cl$^-$-secretion with $EC_{50}$ values of 1.5 mM and 100 μM, respectively.

Figure 3A:
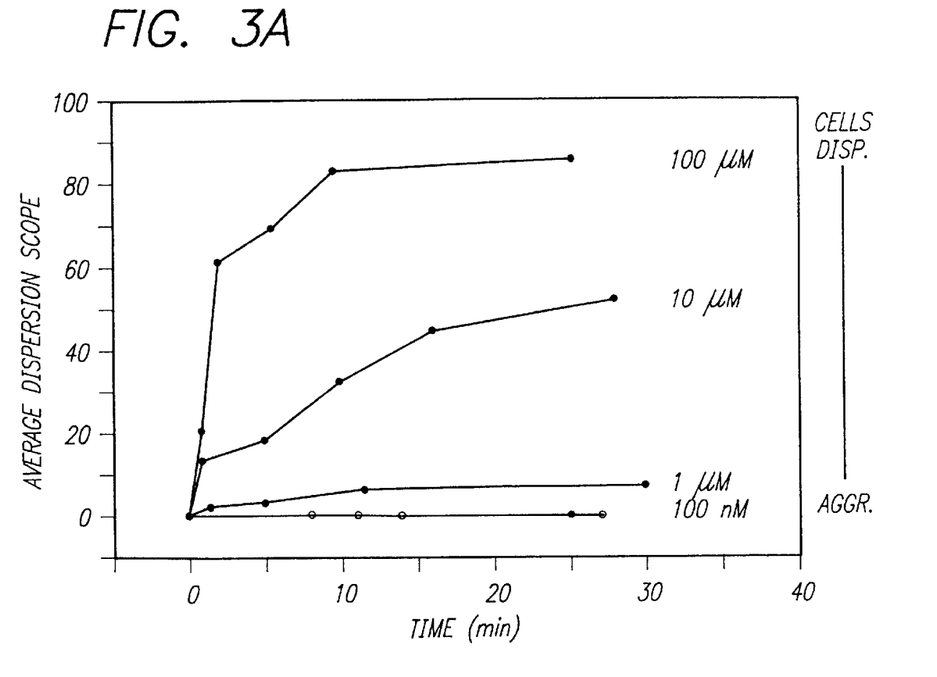
FIG. 3A shows the results of tests demonstrating the ability of $Bt_2cAMP/AM$ to disperse fish dermal chromatophores.
Figure 3B:
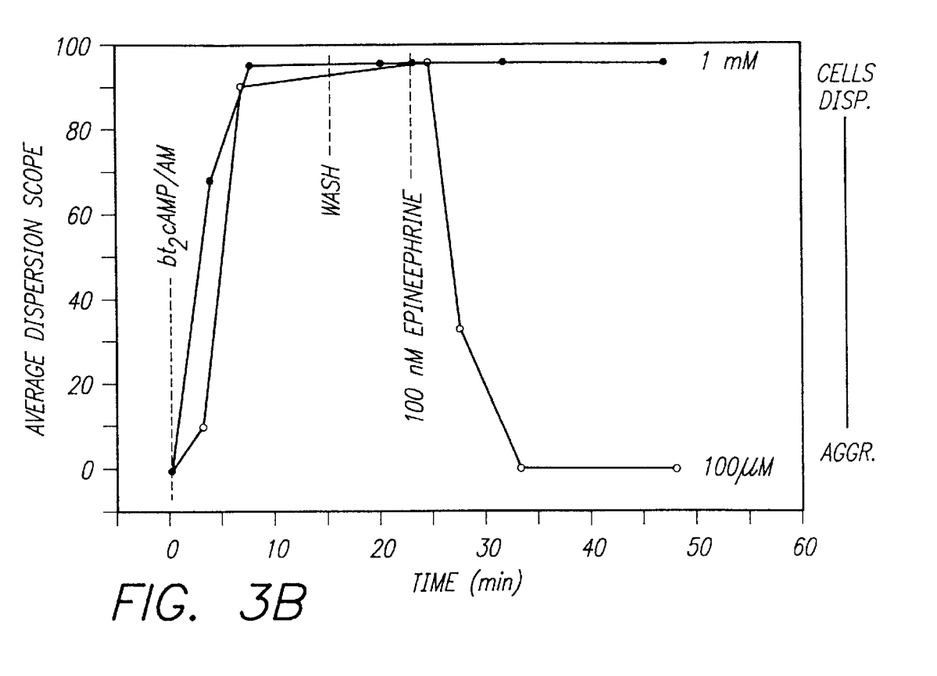
FIG. 3B is a graph showing test results demonstrating the reversibility of the dispersion shown in FIG. 3A.

Fish dermal chromatophores exhibit a tightly regulated movement of pigment granules either inward into a highly aggregated central mass, or outward, dispersing the pigment throughout the cell. In angelfish (*Pterophyllum scalare*) melanophores this movement is microtubule based and cAMP regulated (44,47) but relatively refractory to external cAMP analogs. Melanophores permit a visual single-cell assay for the ability of cAMP analogs to enter cells and mimic cAMP actions. The melanophores were isolated on angelfish scales and the epidermis was stripped off. The 60–100 melanophores per scale were pretreated with an $α_2$-adrenergic agonist to reduce endogenous cAMP and start with full aggregation. Extracellular $Bt_2cAMP/AM$ then caused dispersion of the pigment in a dose-dependent manner (FIG. 3A). A concentration of 100 μM $Bt_2cAMP/AM$ was enough to cause essentially complete dispersal; however, 1 mM gave a slightly faster onset of action and could not be readily reversed by removal of the extracellular $Bt_2cAMP/AM$ and administration of epinephrine, whereas the effect of 100 μM was easily reversed (FIG. 3B). Dispersion was just detectable at 1 μM and half-maximal near 10 μM (FIG. 3A). By comparison, 1 mM $Bt_2cAMP$ was unable to cause any detectable dispersion. Hence the AM ester group increased the potency by more than 1000 in this assay. The effectiveness of $Bt_2cAMP/AM$ shows that the inertness of $Bt_2cAMP$ in melanophores is due to poor permeability rather than susceptibility of Bt-cAMP to phosphodiesterases or selectivity of kinase binding sites for cAMP substitution (48). The preceding examples are summarized in (64).

The preceding strategy for increasing permeability of cAMP and cGMP, i.e. acetoxymethyl esterification in combination with butyryl group masking of the hydroxyl groups, was found not to be effective for inositol phosphates. Acetoxy-methyl esters of inositol triphosphates which had their hydroxy groups blocked with butyryl groups were found to have relatively low potency, perhaps because butyryl esters located between bulky phosphate groups cannot be cleaved by intracellular enzymes. However, if the hydroxyl groups were left unesterified and the phosphates were esterified with acetoxymethyl groups, the resulting compounds had insufficient membrane permeability to enter cells. We found that, in addition to leaving the hydroxyl groups unesterified, it was also necessary to replace the acetoxymethyl groups with more hydrophobic groups in order to provide acceptable cell permeability and subsequent ester cleavage. We discovered that more hydrophobic esters such as, propionyloxymethyl(PM) esters (R=ethyl, R'=H) or butyryloxymethyl(BM) esters (R=propyl, R'=H), permeate the cell membrane at higher rates while still being amenable to cleavage upon entry into the cell.

Inositol phosphate esters in accordance with the present invention have the formula wherein $A_1$ to $A_6$ is H, OH, F or wherein R is an alkyl group having from 2 to 6 carbon atoms and R' is H or $CH_3$ or R is $CH_3$ and R' is $CH_3$ and wherein at least one of $A_1$ to $A_6$ is a phosphoester having the formula set forth above.

Preferred esters are the propionyloxymethyl and butyryloxymethyl esters of: inositol-1,4,5-triphosphate; 3-deoxy-inositol-1,4,5-triphosphate; 3-fluoroinositol-1,4,5-triphosphate; inositol-1,3,4-triphosphate; inositol-1,3,4,5-tetrasphosphate; and inositol-3,4,5,6-tetrasphosphate.

Figure 5:
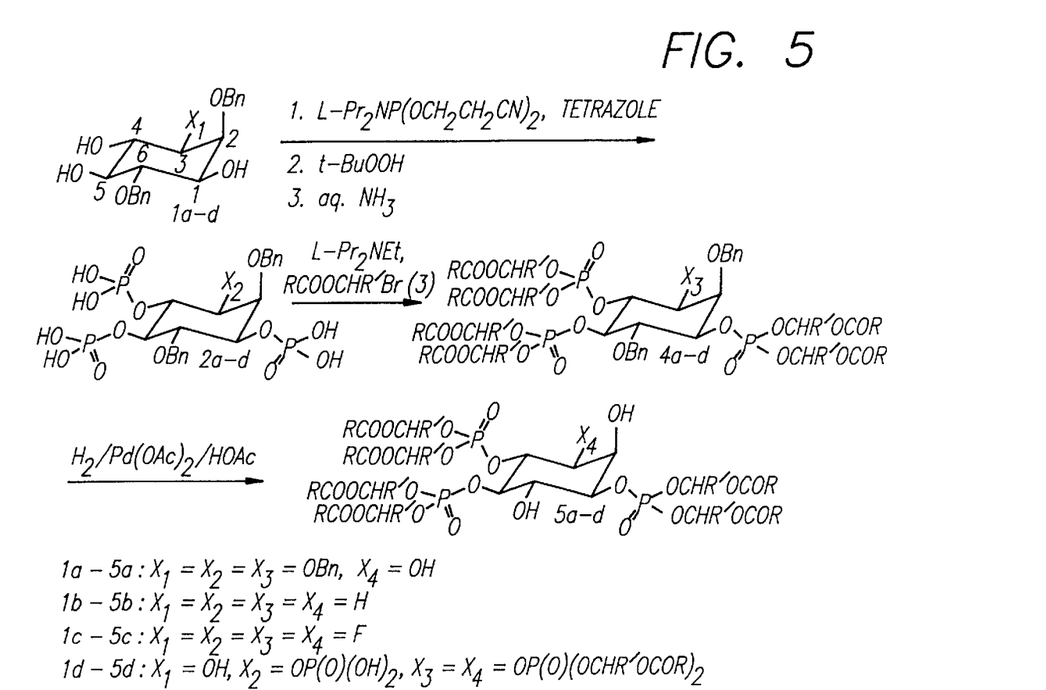
FIG. 5 is a schematic representation of the synthesis of exemplary esters of inositol phosphates.

Examples of synthesis and use of preferred exemplary inositol polyphosphate esters in accordance with the present invention is as follows:

The general synthesis scheme which may be used to make a number of different esters in accordance with the present invention is set forth in FIG. 5.

The synthesis of phosphotriesters with neighboring unprotected hydroxyls is difficult because the phosphates very easily migrate or cyclize into the free hydroxyls. The key is to use benzyl ethers to protect the hydroxyls for as many steps as possible and to find conditions to remove the benzyls at the last stage without affecting the phosphate acyloxyalkyl esters (FIG. 5). Thus in the synthesis of, for example, inositol tri phosphate propionyloxymethyl ester (IP$_3$/PM), the hydroxyls on the 2, 3, and 6-positions are initially protected as benzyl groups. Phosphorylation of 1 with bis($\beta$-cyanoethyl)N,N-diisopropylphosphoramidite, oxidation of the phosphites, and ammonolysis of the cyanoethyl protecting groups affords 2,3,6-tri-O-benzyl-IP$_3$ (2a). Esterification with bromomethyl propionate (3, R=Et, R'=H) gives fully protected inositol trisphosphate (4a). Finally, catalytic hydrogenolysis over palladium acetate in acetic acid provides IP$_3$/PM (5a, R=Et, R'=H) without phosphate migration or cyclization. This general procedure may be used to synthesize other membrane-permeant, intracellularly hydrolyzable esters of IP$_3$ and other important inositol polyphosphates such as 3-deoxy-1,4,5-IP$_3$, 3-fluoro-1,4,5-IP$_3$, 1,3,4-IP$_3$, 1,3,4,5-IP$_4$, and 3,4,5,6-IP$_4$.

A detailed description of the synthesis is as follows:

D-2,3,6-tri-O-benzyl-myo-inositol 1a and D-2,6-di-O-benzyl-myo-inositol 1d, which are known compounds (65, 66), are synthesized from myo-inositol by a modified procedure (for 1a) or as published (for 1d). D-2,3-di-O-benzyl-3-deoxymyo-inositol 1b and D-2,3-di-O-benzyl-3-deoxy-3-fluoro-myo-inositol 1c, may be prepared in two steps from known precursors (67,68), D-1,4,5-tri-O-benzoyl-6-O-benzyl-3-deoxy-myo-inositol (compound 10 in ref. 67) or D-1,4,5-tri-O-benzoyl-6-O-benzyl-3-deoxy-3-fluoro-myo-inositol (compound 5b in ref. 68) respectively. These starting materials may be benzylated with benzyl trichloroacetimidate in the presence of a catalytic amount of trifluoromethanesulfonic acid. Removal of the benzoyl protecting groups with potassium carbonate in methanol overnight affords 1b and 1c, respectively. The experimental procedure outlined in FIG. 5 is similar for 5a, 5b, 5c and 5d. Here we use 5a as an example. All reactions are done under an atmosphere of argon unless otherwise specified.

D-2,3,6-tri-O-benzyl-myo-inositol-1,4,5-tri phosphate (2a), ammonium salt: 65 mg 1a (0.144 mmol) was dissolved in 1 ml dichloromethane and 1 ml acetonitrile. Bis($\beta$-cyanoethyl)-N,N-diisopropylphosphoramidite (69) (180 $\mu$l, 0.65 mmol) was added, followed by 48 mg tetrazole (0.69 mmol) dissolved in 1.2 ml acetonitrile. After stirring at room temperature for 2 hours, the reaction flask was cooled in an ice bath. An excess of t-butyl hydroperoxide (300 $\mu$l of a 5M solution in dichloromethane) was added in one portion. Thirty minutes later, the ice bath was removed and stirring was continued at room temperature for another hour. The solvent was removed under reduced pressure. The remaining syrup was resuspended in the minimum amount of dichloromethane/methanol (12:1). 130 mg of a clear glass was obtained. This material was dissolved in 1.5 ml methanol and mixed with 6 ml concentrated ammonium hydroxide. It was refluxed at 60° C. for 3 hours and the solvent was removed under reduced pressure. The remaining material was used directly for the next step without further purification.

D-2,3,6-tri-O-benzyl-myo-inositol-1,4,5-triphosphate propionyloxymethyl ester (4a). The above material (2a) was suspended in 1 ml acetonitrile and 0.2 ml diisopropylethylamine (DIEA). It was then sonicated for a short interval and the solvent was removed under reduced pressure. This process was repeated a few more times until a homogeneous solution was obtained after adding acetonitrile and DIEA, indicating that the counterions for the phosphate groups had been exchanged from ammonium to diisopropylethylammonium. An excess (~150 $\mu$l) of bromomethyl propionate (3, R=Et, R'=H, prepared as in ref. 70) was then added and left to react for 48 hours. The solvent was removed under vacuum and the remaining syrup was first purified by silica gel flash column chromatography, eluting with ethyl acetate. The pale yellow glass obtained upon evaporation was further purified by HPLC on a C18 reverse-phase column, eluting with 78% methanol in water. 15 mg clear glass was obtained, 10% overall yield from 1a. $^1$H-NMR (CDCl$_3$): $\delta$=1.1 (m, 18H), 2.2–2.45 (m, 12H), 3.5 (dd, 1H,J=12 Hz, 2 Hz), 4.05 (t, 1H, J=11.2 Hz), 4.3–4.5 (m, 3H), 4.7–4.9 (m, 7H), 5.3–5.7 (m, 12H), 7.2–7.5 (m, 15H), FAB MS m/z (M+Cs)$^+$. Calculated: 1339.2293. Observed: 1339.2261.

D-myo-inositol-1,4,5-triphosphate propionyloxymethyl ester (5a, R=Et, R'=H). 15 mg 4a was dissolved in 2 ml glacial acetic acid. 20 mg palladium acetate and a catalytic amount of trifluoroacetic acid was added. The mixture was stirred under 1 atm hydrogen gas at a temperature below 20° C. to minimize phosphate triester migration. After 4 hours of hydrogenation, the catalyst was filtered off and the acetic acid was lyophilized. 10 mg clear glass was obtained. $^1$H-NMR (CD30D): $\delta$=1.2 (m, 18H), 2.4 (m, 12H), 3.7 (dd, 1H, J=9.9 Hz), 2.4 Hz), 4.0 (t, 1H, J=9.3 Hz), 4.2–4.4 (m, 3H), 4.65 (q, 1H, J=8.4 Hz), 5.7 (m, 12H).

D-myo-inositol-1,4,5-triphosphate butyryloxymethyl ester (5a, R=Pr, R'=H) was prepared identically but with bromomethyl butyrate (3, R=Pr, R'=H) in place of bromomethyl propionate. $^1$H-NMR (CD30D): $\delta$=0.95 (m, 18H), 1.7 (m, 12H), 2.4 (m, 12H), 3.7 (dd, 1H, J=9.9 Hz, 2.4 Hz), 4.0 (t, 1H, J=9.3 Hz), 4.2–4.4 (m, 3H), 4.65 (q, 1H, J=8.4 Hz), 5.7 (m, 12H). FAB MS m/z (M+Cs)$^+$. Calculated: 1153.1824. Observed: 1153.1850.

Biological Applications of IP$_3$/PM and IP$_3$/BM

Figure 6:
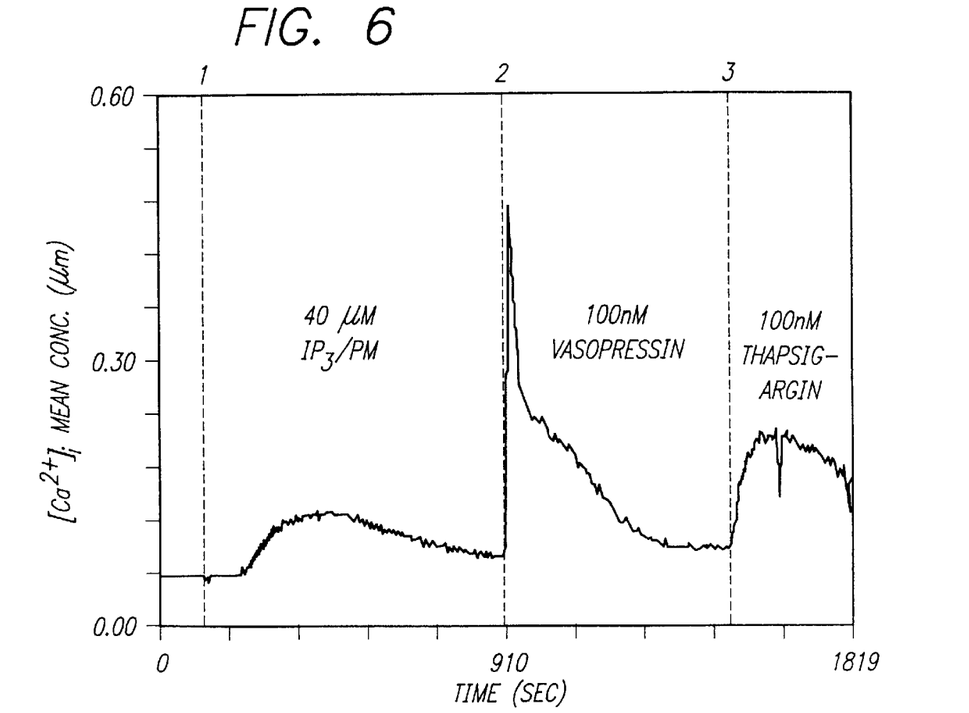
FIG. 6 depicts test results showing permeation of inositol triphosphate propionyloxymethyl ester ($IP_3$/PM) into REF-52 fibroblast cells.

The best-established biological effect of IP$_3$ is to release Ca$^{2+}$ from internal stores (26), so IP$_3$/PM (5a, R=Et, R'=H) was tested by imaging cytosolic free Ca$^{2+}$ levels in single REF-52 fibroblasts using standard methodology (58). Cells were loaded with the Ca$^{2+}$-indicator fura-2 and viewed by fluorescence excitation ratioing. IP$_3$/PM (40 $\mu$M) was applied extracellularly while monitoring cytosolic Ca$^{2+}$ concentrations. As shown in FIG. 6, the Ca$^{2+}$ concentration increased rapidly after addition of IP$_3$/PM (vertical dotted line labeled 1). Subsequent addition of vasopressin (vertical dotted line labeled 2), a well-known Ca$^{2+}$-releasing hormone (59) had much less effect than normal. This occlusion demonstrates that IP$_3$/PM had already partially exhausted the same pathways to elevate Ca$^{2+}$ as utilized by a physiological agonist, vasopressin.

Figure 7:
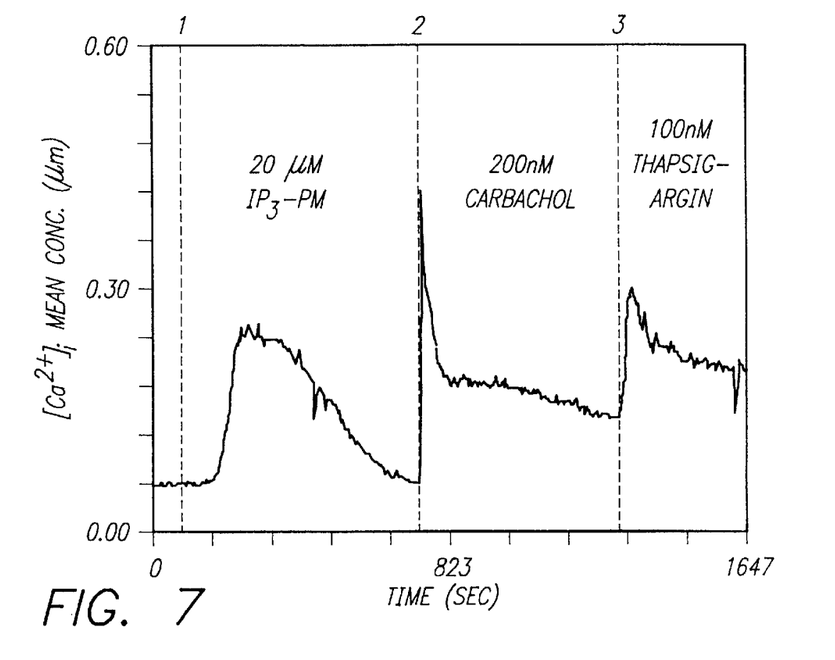
FIGS. 7 depicts test results showing permeation of $IP_3$/PM into astrocytoma cells at a dose of 20 $\mu$m in a medium containing extracellular $Ca^{2+}$.

Biological tests on 1321N1 astrocytoma cells were performed similarly to the tests on REF-52 cells (71). The results of the tests are shown in FIG. 7. The concentration of Cytosolic free Ca$^{2+}$ (ordinate, in units of PM) in fura-2-loaded 1321N1 astrocytoma cells is shown as a function of time (abscissa, in units of seconds). At the dotted vertical line labeled 1, 20 $\mu$M inositol-1,4,5-triphosphate propionyloxymethyl ester (5a, R=Et, R'=H) was added. A sizable elevation of cytosolic Ca$^{2+}$ was observed after about 100 second delay. Subsequently the cells could respond to carbachol (200 $\mu$M, delivered at the dotted vertical line labeled 2), a drug that stimulates the endogenous generation of inositol-1,4,5-triphosphate. However, the response to carbachol is depressed by the prior treatment with the inositol-1,4,5-triphosphate propionyloxymethyl ester. Likewise the Ca$^{2+}$ response to thapsigargin (100 nM, delivered at the dotted vertical line labeled 3), another drug that releases stored Ca$^{2+}$, is depressed.

A test similar to the one shown in FIG. 7 was conducted except that the medium lacked extracellular Ca$^{2+}$ and a dose of 60 $\mu$M inositol-1,4,5-triphosphate propionyloxymethyl ester was added at the dotted vertical line labeled 1. The results of the test are shown in FIG. 8. A sizable elevation of cytosolic Ca$^{2+}$ was observed after about a 50 second delay.

Because no extracellular $Ca^{2+}$ was present, this response must have represented release from intracellular $Ca^{2+}$ stores. Subsequently the cells' response to carbachol (200 μM, delivered at the dotted vertical labeled 2) was greatly depressed by the prior treatment with the inositol-1,4,5-triphosphate propionyloxymethyl ester. The much greater degree of inhibition of the carbachol response compared to the previous example (FIG. 7) is due to the higher dose of the inositol-1,4,5-triphosphate propionyloxymethyl ester and the absence of extracellular $Ca^{2+}$, which reduces refilling of $Ca^{2+}$ stores.

In a further example, the same test as set forth above was conducted with astrocytoma cells, except that 2 μM inositol-1,4,5-triphosphate butyryloxymethyl ester (5a, R=Pr, R'=H) was used instead of the propionyloxymethyl ester.

Figure 9:
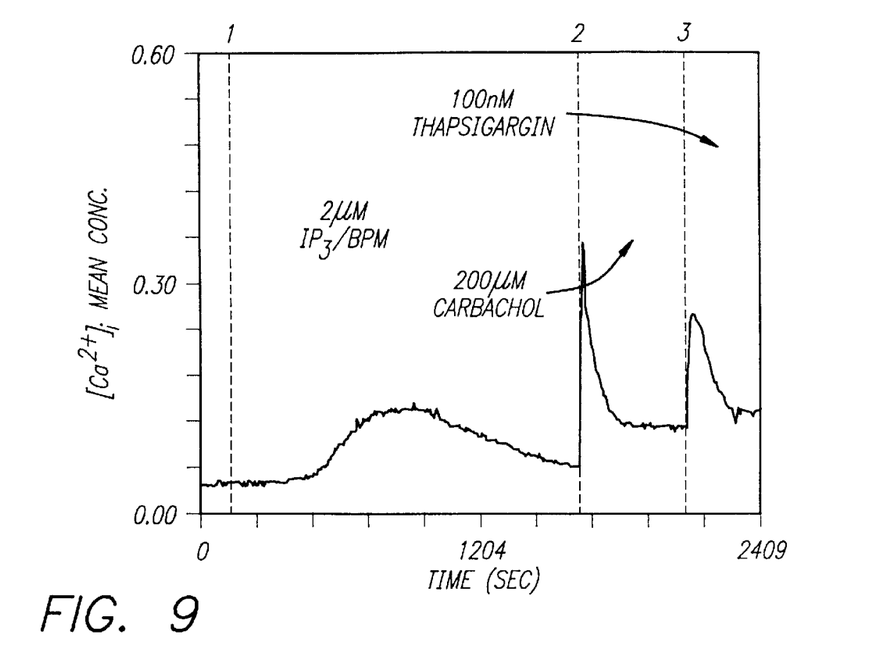
FIG. 9 depicts test results showing permeation of inositol triphosphate butyryloxymethyl ester ($IP_3$/BM) into astrocytoma cells at a dose of 2 $\mu$m in a medium containing extracellular $Ca^{2+}$.

The test results are shown in FIG. 9. The butyryloxymethyl ester is somewhat more potent but its effects are slower to appear and decay.

The above biological results show that neutral, hydrophobic, membrane-permeant derivatives of inositol phosphates can be synthesized and show the expected biological activity when applied extracellularly to intact REF-52 fibroblasts and astrocytoma cells. $IP_3$/PM released $Ca^{2+}$ from internal stores, as would be expected for an agent that mimicked $IP_3$.

Permeant inositol polyphosphate derivatives as described above are useful to investigate longer-term effects on cells not mediated through cytosolic $[Ca^{2+}]_i$. For example, possible effects on protein synthesis, phosphorylation, proliferation (49), or gene expression are relatively difficult to study on microinjected, patch-clamped, or permeabilized cells.

Inositol polyphosphates are among the most ubiquitous and important intracellular second messengers. They are essential for hormone secretion and action, smooth muscle contraction, immune activation, fertilization, and neuronal function. As previously mentioned, the best known inositol polyphosphate is myo-inositol-1,4,5-triphosphate ($IP_3$), which acts by releasing $Ca^{2+}$ from intracellular stores. $IP_3$ undergoes further metabolism to a series of inositol polyphosphates of largely unknown biochemical function. A major problem in investigating the biological functions of inositol polyphosphates is their membrane impermeability. All existing techniques for delivering exogenous inositol polyphosphates into cells require puncture of their plasma membranes by techniques that jeopardize the cells' viability and are often applicable only to single cells. The inositol polyphosphate derivatives in accordance with the present invention provide a solution of this problem because they are membrane-permeant and they regenerate into biologically active inositol polyphosphates once inside the cell.

The acyloxyalkyl esters of phosphate-containing second messengers in accordance with the present invention may be used in any situation where it is desirable to introduce the second messenger into a cell without puncturing the cell membrane or otherwise adversely affecting the cell. The present invention is useful as a replacement for the existing methods which rely on microinjection, patch-clamp and electroporation techniques to introduce phosphate-containing second messengers into cells.

The acyloxyalkyl esters are introduced into the selected cells by simply exposing the cells to the esters in cell growth media or other suitable solution. The amount of ester which is introduced into the cell can be controlled by reducing or increasing the concentration of ester present in the cell growth media. The amount of ester which permeates into the cell may also be controlled by limiting the amount of time that the cells are left exposed to the ester.

Having thus described exemplary embodiments of the present invention, it will be understood by those skilled in the art that the within disclosures are exemplary only and that the invention is only limited by the following claims.

BIBLIOGRAPHY

1. Hardie, D. G.(1991) *Biochemical Messengers: Hormones, Neurotransmitters and Growth Factors*, Champman & Hall, London.
2. Robinson, G. A., Butcher, R. W., and Sutherland, E. W. (1971) *Cyclic AMP*, Academic Press, New York.
3. Corbin, J. D., Johnson, R. A., eds (1988) *Methods in Enzymology: Initiation and Termination of Cyclic Nucleotide Action*, Academic Press, Inc., San Diego.
4. Goy, M. F.(1991) *Trends Neurosci.* 14, 293–299.
5. Berridge, M. J. and Irvine, R. F. (1989) *Nature* 341, 197–205.
6. Meyer, R. B., Jr. (1980) in *Burger's Medicinal Chemistry* (Wolff, M. E., ed.) pp. 1201–1224, Wiley, New York.
7. Polokoff, M. A., Bencen, G. H., Vacca, J. P., deSolms, S. J., Young, S. D., and Huff, J. R. (1988) *J. Biol. Chem.* 263, 11922–11927.
8. Henion, W. F., Sutherland, E. W., and Posternak, T. (1967) *Biochim. Biophys. Acta* 148,106–113.
9. Roche, E. B., ed. (1987) *Bioreversible Carriers in Drug Design* Pergamon Press, New York.
10. Falbriard, J. -G., Posternak, T., and Sutherland, E. W. (1967) *Biochim. Biophys. Acta* 148, 99–105.
11. Jansen, A. B. A. and Russell, T. J. (1965) *J. Chem. Soc.* 2127–2132.
12. Tsien, R. Y.(1981) *Nature* 290, 527–528.
13. Grynkiewicz, G., Poenie, M., and Tsien, R. Y. (1985) *J. Biol. Chem.* 260, 3440–3450.
14. Tsien, R. Y.(1989) *Methods Cell Biol.* 30, 127–156.
15. Srivastva, D. N. and Farquhar, D. (1984) *Bioorg. Chem.* 12, 118–129.
16. Iyer, R. P., Phillips, L. R., Biddle, J. A., Thakker, D. R., Egan, W., Aoki, S., and Mitsuga, H. (1989) *Tetrahedron Lett.* 30, 7141–7144.
17. Sastry, J. K., Nehete, P. N., Khan, S., Nowak, B. J., Plunkett, W., Arlinghaus, R. B., and Farquhar, D. (1992) *Mol. Pharmacol.* 41, 441–445.
18. Freed, J. J., Farquhar, D., and Hompton, A. (1989) *Biochem. Pharmacol.* 38, 3193–3198.
19. Saperstein, R., Vicario, P. P., Strout, H. V., Brady, E., Slater, E. E., Greenlee, W. J., Ondeyka, D. L., Patchett, A. A., and Hangauer, D. G. (1989) *Biochemistry* 28, 5694–5701.
20. Walker, J. W., Reid, G. P., McCray, J. A., and Trentham, D. R. (1988) *J. Am. Chem. Soc.* 110, 7170–7177.
21. Nerbonne, J. M., Richard, S., Nargeot, J., and Lester, H. A. (1984) *Nature* 310, 74–76.
22. Engels, J. and Schlaeger, E. -J. (1977) *J. Med. Chem.* 20, 907–911.
23. Walker, J. W., Feeney, J., and Trentham, D. R. (1989) *Biochemistry* 28, 3272–3280.
24. Gurney, A. M. and Lester, H. A. (1987) *Physiol. Rev.* 67, 583–617.
25. McCray, J. A. and Trentham, D. R. (1989) *Annu. Rev. Biophys. Biophys. Chem.* 18, 239–270.
26. Berridge, M. J. and Irvine, R. F. (1989) *Nature* 341, 197–205.
27. Irvine, R. F. and Moor, R. M. (1986) *Biochem. J.* 240, 917–920.
28. Irvine, R. F. (1990) *FEBS Letters* 263, 5–9.
29. Morris, A. P., Gallacher, D. V., Irvine, R. F., and Petersen, O. H. (1987) *Nature* 330, 653–655.

30. Changya, L., Gallacher, D. V., Irvine, R. F., Potter, B. V. L., and Petersen, O. H. (1989) *J. Membrane Biol.* 109, 85–93.
31. Boynton, A. L., Dean, N. M., and Hill, T. D. (1990) *Biochem. Pharmacol.* 40, 1933–1939.
32. Hill, T. D., Dean, N. M., and Boynton, A. L. (1988) *Science* 242, 1176–1178.
33. Crossley, I., Swann, K., Chambers, E., and Whitaker, M. (1988) *Biochem. J.* 252, 257–262.
34. Snyder, P. M., Krause, K. -H., and Welsh, M. J. (1988) *J. Biol. Chem.* 263, 11048–11051.
35. Tsien, R. W. and Tsien, R. Y. (1990) *Annu. Rev. Cell Biol.* 6, 715–760.
36. Bird, G. St J., Rossier, M. F., Hughes, A. R., Shears, S. B., Armstrong, D. L., and Putney, Jr., J. W. (1991) *Nature* 352, 162–165.
37. Balla, T., Sim, S. S., Iida, T., Choi, K. Y., Catt, K. J., and Rhee, S. G. (1991) *J. Biol. Chem.* 266, 24719–24726.
38. Grynkiewicz, G. and Tsien, R. Y. (1987) *Pol. J. Chem.* 61, 443–447.
39. Adams, S. R., Harootunian, A. T., Buechler, Y. J., Taylor, S. S., and Tsien, R. Y. (1991) *Nature* 349, 694–697.
40. Dharmsathaporn, K., Mandel, K. G., Masui, H., and McRoberts, J. A. (1985) *J. Clin. Invest.* 75, 462–470.
41. Madara, J. and Dharmsathaporn, K. (1985) *J. Cell Biol.* 101, 2124–2133.
42. Dharmsathaporn, K., Mandel, K. G., McRoberts, J. A., Tisdale, L. D., and Masui, H. (1984) *Am. J. Physiol.* 264, G204–G208.
43. McRoberts, J. A. and Barrett, K. E. (1989) *Modern Cell Biology* (Mathi, K. S. and Valeulich, J. D., eds) pp. 235–265, Alan R. Liss, Inc., New York.
44. Sammak, P. J., Adams, S. R., Harootunian, A. T., Schliwa, M., and Tsien, R. Y. (1992) *J. Cell Biol.* 117, 57–72.
45. Taylor, S. S., Buechler, J. A., and Yonemoto, W. (1990) *Annu. Rev. Biochem.* 59, 971–1005.
46. Barrett, K. E. and Dharmsathaporn, K. (1991) *Textbook of Gastroenterology* (Yamada, T., ed) pp. 265–294, J. B. Lippincott Co., Philadelphia.
47. Schliwa, M. (1975) *Microtubules and Microtubule Inhibitors* (Borgers, M. and de Brabender, M., eds) pp. 215–228, Elsevier Science, Amsterdam.
48. Beebe, S. J., Blackmore, P. F., Chrisman, T. D., and Corbin, J. D. (1988) *Methods Enzymol.* 159, 118–139.
49. Smirnova, L. I., Malenkovskaya, N. A, Preddoditelev, D. A., and Nifant'ev, E. E. (1980) *Zh. Org. Khim.* 16, 1011–1019.
50. Angyal, S. J. and Tate, M. E. (1965) *J. Chem. Soc.* 6949–6955.
51. Tegge, W. (1986) Ph.D. Thesis University of Bremen-FRG.
52. Lee, H. W. and Kishi, Y. (1985) *J. Org. Chem.* 50, 4402–4404.
53. Billington, D. C., Baker, R., Kulagowski, J. J., Mawer, I. M., Vacca, J. P., deSolms, S. J., and Hugg, J. R. (1989) *J. Chem. Soc. Perkin Trans.* 1 1423–1429.
54. Baudin, G., Glanzer, B. I., Swaminathan, K. S., and Vaselia, A. (1988) *Helv. Chim. Acta* 71, 1367–1378.
55. Tegge, W. and Ballou, C. E. (1989) *Proc. Natl. Acad. Sci. USA* 86, 94–98.
56. Perich, J. W. and Johns, R. B. (1987) *Tetrahedron Lett.* 28, 101–102.
57. Thastrup, O., Cullen, P. J., Drobak, B. K., Hanley, M. R., and Dawson, A. P. (1990) *Proc. Natl. Acad. Sci. USA* 87, No. 7, 2466–2470.
58. Tsien, R. Y. and Harootunian, A. T. (1990) *Cell Calcium* 11, 93–109.
59. Harootunian, A. T., Kao, J. P. Y., Paranjape, S., Adams, S. R., Potter, B. V. L., and Tsien, R. Y. (1991) *Cell Calcium* 12, 153–164.
60. Harootunian, A. T., Kao, J. P. Y., Paranjape, S., and Tsien, R. Y. (1991) *Science* 251, 75–78.
61. Finch, E. A., Turner, T. J., and Goldin, S. M. (1991) *Scient* 252, 443–446.
62. Kuno, M. and Gardner, P. (1987) *Nature* 236, 301–304.
63. Penner, R., Matthews, G., and Neher, E. (1988) *Nature* 334, 499–504.
64. Schultz, C. et al. (1993) *Journal of Biological Chemistry* Vol. 268, No. 9, 6316–6322.
65. Oozaki, S. et al., *Tetrahedron Lett.* 27 (1986), 3157; Dreef, C. E. et al., *Rec. Trav. Chim. Pays-Bas.* 107 (1988), 395.
66. Billington, D. C. et al., *J. Chem. Soc. Chem. Communications* (1987), 1011; Baudin, G. et al., *Helv. Chim. Acta* 71 (1988) 1367.
67. Kozikowski, A. P. et al., *J. Am. Chem. Soc.* 115 (1993), 4429.
68. Kozikowski, A. P. et al., *J. Am. Chem. Soc.* 112 (1990), 7403.
69. Bannwarth, W. et al., *Helv. Chim. Acta.* 70 (1987), 175.
70. Euranto, E. K. et al., *Acta. Chem. Scand.* 20 (1966), 1273.
71. Randriamampita, C and Tsien, R. Y. (1993) *Nature* 364:809–814.

What is claimed is:

1. A compound having the formula wherein $A_1$ to $A_6$ is H, OH, F or wherein R is an alkyl group having from 2 to 6 carbon atoms and R' is H or $CH_3$ or R is $CH_3$ and R' is $CH_3$ and wherein at least one of $A_1$ to $A_6$ is a phosphoester having the formula set forth above.

2. A compound according to claim 1 wherein $A_1$, $A_4$ and $A_5$ are wherein R is an alkyl group having from 2 to 6 carbon atoms and R' is H or R is $CH_3$ and R' is $CH_3$.

3. A compound according to claim 1 wherein $A_1$, $A_3$, $A_4$ and $A_5$ are wherein R is an alkyl group having from 2 to 6 carbon atoms and R' is H or R is $CH_3$ and R' is $CH_3$.

4. A compound according to claim 1 wherein $A_3$, $A_4$, $A_5$ and $A_6$ are wherein R is and alkyl group having from 2 to 6 carbon atoms and R' is H or R is $CH_3$ and R' is $CH_3$.

5. A compound according to claim 2 wherein R is ethyl or propyl and R' is H.

6. A compound according to claim 3 wherein R is ethyl or propyl and R' is H.

7. A compound according to claim 2 wherein $A_3$ is H and $A_2$ and $A_6$ are OH.

8. A compound according to claim 2 wherein $A_3$ is F and $A_2$ and $A_6$ are OH.

9. A compound according to claim 5 wherein $A_3$ is H and $A_2$ and $A_6$ are OH.

10. A compound according to claim 5 wherein $A_3$ is F and $A_2$ and $A_6$ are OH.

11. A method for introducing a compound into a cell without disrupting the cell membrane, said method comprising the step of contacting said cell with a compound having the formula wherein $A_1$ to $A_6$ is H, OH, F or wherein R is an alkyl group having from 2 to 6 carbon atoms and R' is H or $CH_3$ or R is $CH_3$ and R' is $CH_3$, wherein at least one of $A_1$ to $A_6$ is a phosphoester having the formula set forth above and wherein said cell is contacted with said compound under conditions such that said compound enters said cell without disrupting the cell membrane.

12. A method according to claim 11 wherein $A_1$, $A_4$ and $A_5$ are wherein R is an alkyl group having from 2 to 6 carbon atoms and R' is H or R is $CH_3$ and R' is $CH_3$.

13. A method according to claim 11 wherein $A_1$, $A_3$, $A_4$ and $A_5$ are wherein R is an alkyl group having from 2 to 6 carbon atoms and R' is H or R is $CH_3$ and R' is $CH_3$.

14. A method according to claim 11 wherein $A_3$, $A_4$, $A_5$ and $A_6$ are wherein R is and alkyl group having from 2 to 6 carbon atoms and R' is H or R is $CH_3$ and R' is $CH_3$.

15. A method according to claim 12 wherein R is ethyl or propyl and R' is H.

16. A method according to claim 13 wherein R is ethyl or propyl and R' is H.

17. A method according to claim 12 wherein $A_3$ is H and $A_2$ and $A_6$ are OH.

18. A method according to claim 12 wherein $A_3$ is F and $A_2$ and $A_6$ are OH.

19. A method according to claim 15 wherein $A_3$ is H and $A_2$ and $A_6$ are OH.

20. A method according to claim 15 wherein $A_3$ is F and $A_2$ and $A_6$ are OH.

* * * * *